United States Patent [19]

Rose et al.

[11] 4,260,258
[45] Apr. 7, 1981

[54] COMPACT, RUGGED SENSOR FOR OPTICAL MEASUREMENT OF THE SIZE OF PARTICLES SUSPENDED IN A FLUID

[75] Inventors: Dennis H. Rose, Claremont; Val E. Davidson, Glendora, both of Calif.

[73] Assignee: Pacific Scientific Company, Montclair, Calif.

[21] Appl. No.: 933,627

[22] Filed: Aug. 14, 1978

[51] Int. Cl.³ ............................................. G01N 15/02
[52] U.S. Cl. ................................... 356/335; 250/573; 356/246
[58] Field of Search ................ 356/335, 436, 437–442; 250/573, 576, 246

[56] References Cited

U.S. PATENT DOCUMENTS

| | | | |
|---|---|---|---|
| 3,812,482 | 5/1974 | Clark | 250/573 X |
| 3,823,320 | 7/1974 | Ledoux | 356/335 |
| 3,879,129 | 4/1975 | Inoux | 356/335 |
| 3,893,766 | 7/1975 | Hogg | 356/335 X |
| 3,910,702 | 10/1975 | Corll | 356/337 X |
| 3,924,951 | 12/1975 | Dittrich | 356/335 |
| 3,932,762 | 1/1976 | Moser | 356/335 X |
| 3,941,479 | 3/1976 | Whitehead | 356/335 |
| 3,952,207 | 4/1976 | Leschonski et al. | 250/573 |
| 3,973,852 | 8/1976 | Moore et al. | 250/573 X |
| 3,984,307 | 10/1976 | Kamentsky et al. | 356/39 X |

FOREIGN PATENT DOCUMENTS

| | | | |
|---|---|---|---|
| 666997 | 11/1938 | Fed. Rep. of Germany | 356/442 |
| 679792 | 9/1952 | United Kingdom | 250/576 |
| 140250 | 1/1960 | U.S.S.R. | 250/573 |

*Primary Examiner*—John K. Corbin
*Assistant Examiner*—Bruce Y. Arnold
*Attorney, Agent, or Firm*—Knobbe, Martens, Olson, Hubbard & Bear

[57] ABSTRACT

A compact, rugged sensor for use in the measurement of particle sizes in a fluid stream is disclosed. The sensor permits the use of a light emitting diode as a light source by mounting a high grade optical system with its focal point at the point light source provided by the light emitting diode to collimate the generated light. This collimated light passes through an aperture formed in one dimension by the width of the fluid flow stream and formed in a second perpendicular dimension by a narrow transparent slit in an otherwise opaque shield adjacent the fluid flow stream. The collimated light source, together with the use of the flow stream as a light path boundary, substantially increases the accuracy of the sensor. All of this is accomplished in conjunction with a solid state light emitting diode source which permits the sensor to be used in shock and vibration environments which would have prohibited particle measurement using prior art sensors.

18 Claims, 9 Drawing Figures

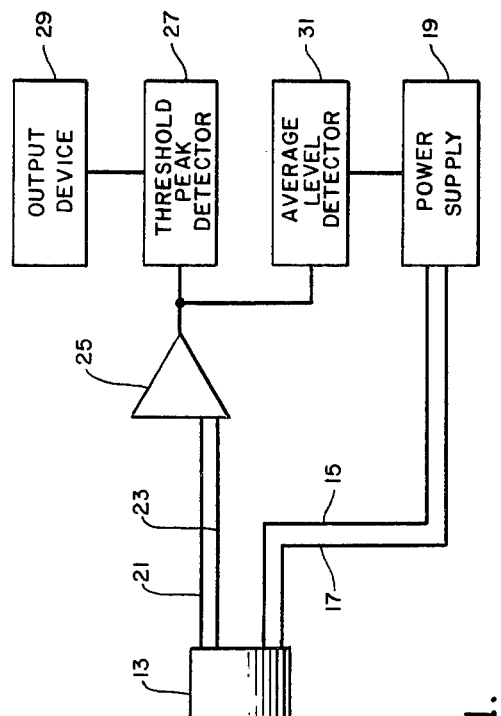
FIG. 1.
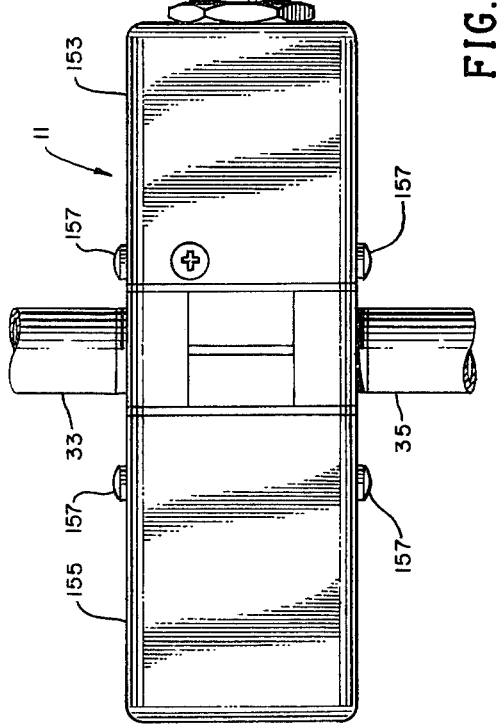
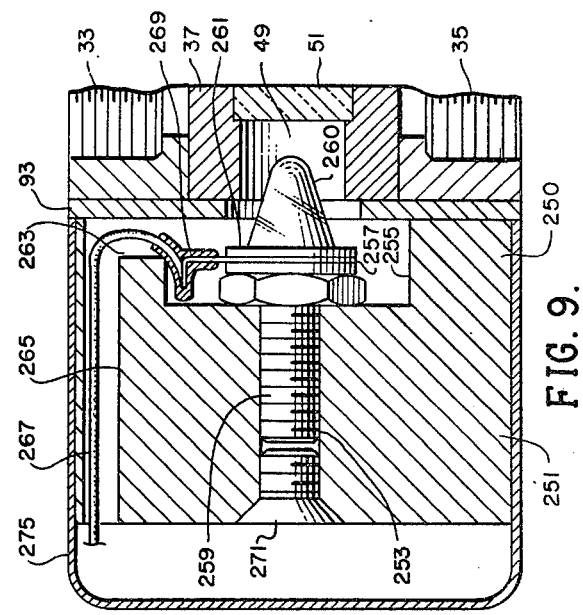
FIG. 9.
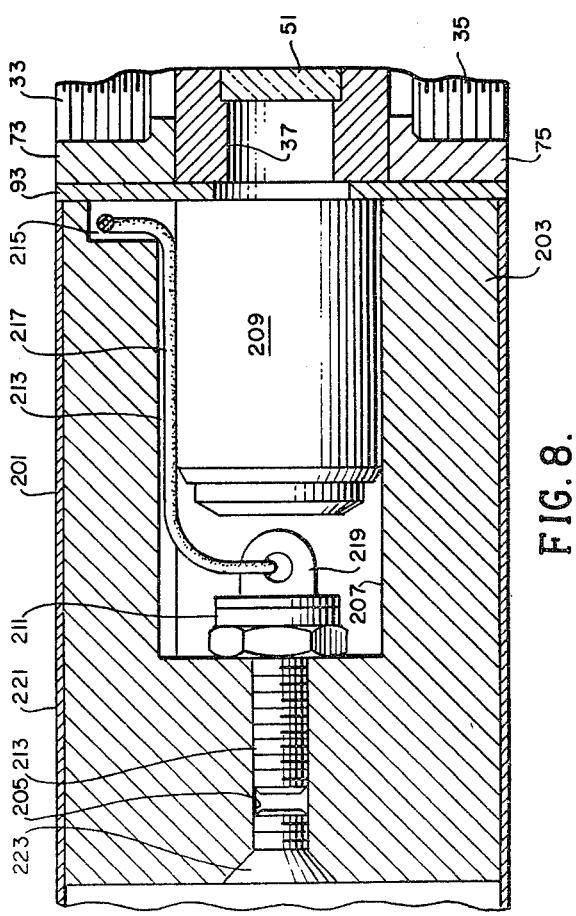
FIG. 8.

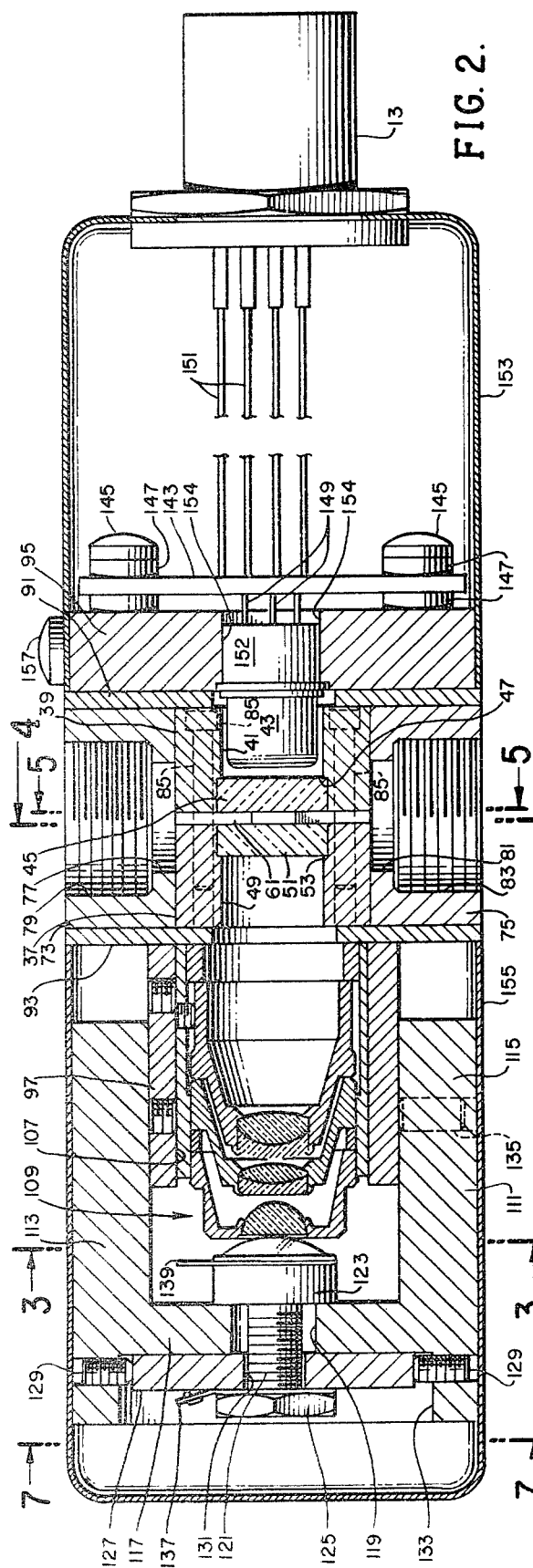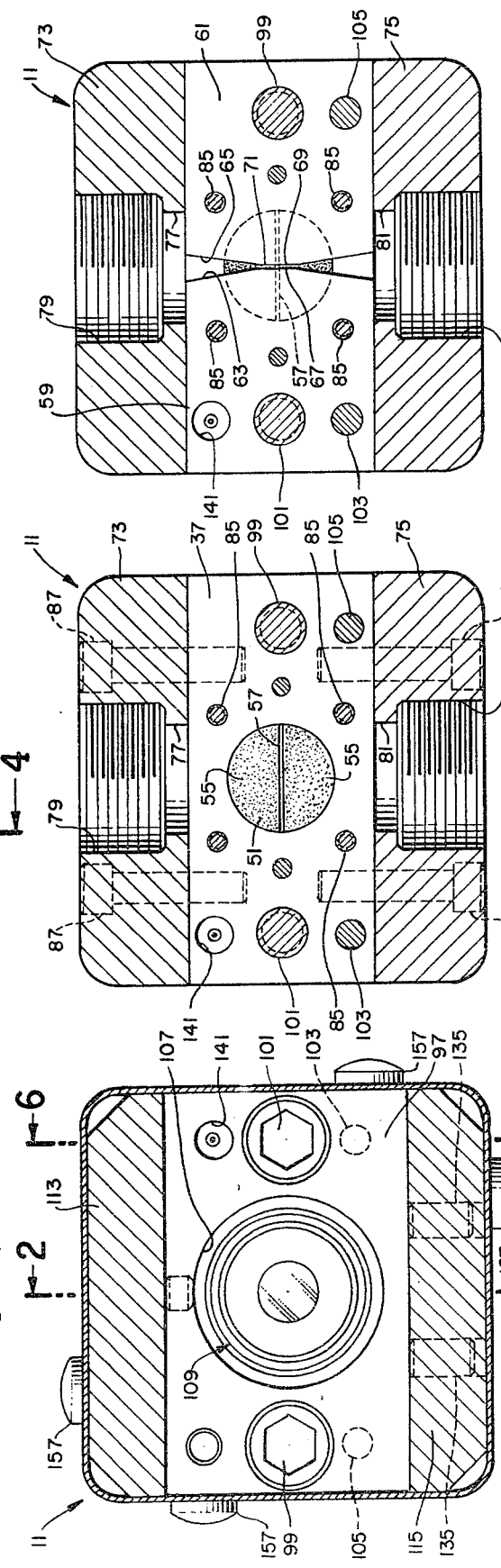

FIG. 6.
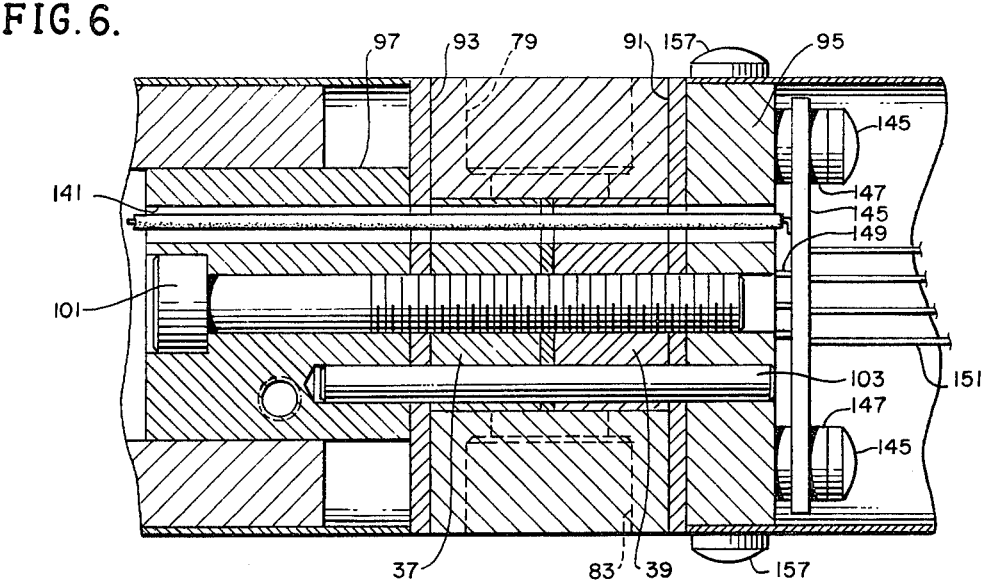
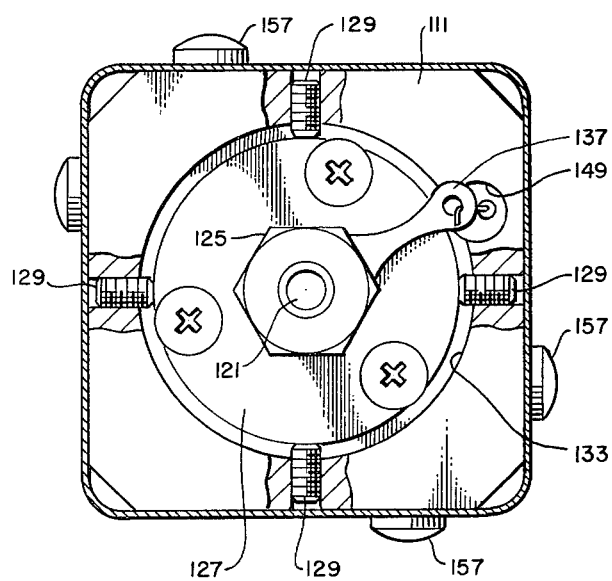
FIG. 7.

COMPACT, RUGGED SENSOR FOR OPTICAL MEASUREMENT OF THE SIZE OF PARTICLES SUSPENDED IN A FLUID

BACKGROUND OF THE INVENTION

The present invention relates to particle size measurement devices, and devices used for counting particles in fluid streams wherein the particles are discriminated on the basis of their size.

More specifically, the present invention pertains to a sensing element used in such systems, the sensing element comprising a light source and light sensitive element positioned on opposite sides of a fluid flow channel. Particles carried by a fluid stream in the flow channel cast a shadow on the light sensitive element, which shadow causes a change in the output signal level from the light sensitive device. By utilizing sensitive, well known prior art signal detectors, the change in this signal can be correlated with a given particle size, and thus particles of various sizes can be measured and counted, the detector signal being supplied to a discriminator circuit which divides the particles into size groups.

While the state of the particle size detecting art is quite advanced, numerous problems have continued unsolved in prior art devices. These problems both limit the permissible environment in which the sensors may be utilized and, at the same time, limit the sensor accuracy. It will be understood by those skilled in the art that particle size discriminating devices, such as those of the present invention, are used in a wide variety of applications. For example, these devices are used for monitoring the quantity and size of impurities in liquid streams to determine when liquids meet cleanliness specifications. They are also used in the production of powders and granulated material to monitor grain size and size distribution. Other uses for the equipment are well known and are limited only by the requirement that the particles to be measured must be carried past the light source and sensing elememt in a fluid or air stream and must be small enough to pass through the flow channel provided between these elements.

In the past there has been a requirement for compromise between the smallest particle sizes which could be measured by such devices and the accuracy and reliability of the devices. As smaller and smaller particle sizes are measured, the light flow path is commonly also reduced in cross-sectional area. For a given light sensor sensitivity (and accepting the fact that the detector signal level, and the changes in detector signal level during measurement, must all be above ambient electrical noise levels), there is a requirement that the light source be made as bright as possible. This, in general, has required, in all practical applications, that the light souce be a high intensity filament bulb. Such bulbs, of course, are subject to fatigue and failure in shock or vibration environments and this fact, by itself, has significantly limited the permissible applications for, and the reliability of sensors.

The use of filament sources (which are not point light sources), has significantly reduced the ability of any lens systems to accurately collimate the light source. Therefore, light passing through the flow channel has generally not been a collimated parallel beam of light, but rather a converging or diverging light pattern. Either of these patterns substantially reduces the accuracy of the measurement system, since the ability of a particular sized particle to cast a particular sized shadow on the light sensor is dependent upon the parallel nature of the light beam. A filament source, particularly in a high intensity bulb, has a relatively large physical size, which prohibits accurate collimation.

Prior to the present invention, no satisfactory solution has been found which both permitted highly accurate, highly dependable size measurement of small particles, while at the same time providing a sensor structure which was operable in vibration and shock environments.

SUMMARY OF THE INVENTION

The present invention provides a solution to these and other problems associated with prior art sensing systems by accurately collimating the light provided by a point source, namely a light emitting diode, and passing this light through a light beam path which is defined by the opposite walls of the fluid flow channel in one axis and by a transparent slit in an otherwise opaque wall of the flow channel in a second axis. This combination of elements produces a highly accurate particle size measuring device which is rugged in construction, a combination not heretofore possible.

More specifically, the present invention permits the adjustable mounting of a relatively high intensity light emitting diode at the focal point of a short focal length collimating lens system provided by the objective lens assembly of a microscope. Such a lens system permits accurate collimation of light from the light emitting diode in a relatively short distance so that the sensor of the present invention can be made relatively compact. The collimated light illuminates a window in the fluid and particle flow path. This window is provided by a pair of shims located between flat plate members, these shims determining the width of the flow path. The window dimension in a direction perpendicular to the flow path is provided by a transparent line or slit in an opaque side wall of the flow channel. The collimated light enters this window as a parallel beam and exits a window on the opposite side of the flow channel. Thus, all of the light passing through the flow channel is a parallel beam so that shadows falling on the light sensing element, such as a photo diode, on the opposite side of the flow path, accurately depict the size of particles in the flow channel.

The use of the microscope objective lens for collimating a relatively low level point light source, such as a light emitting diode, permits, surprisingly, high enough light intensities through the beam window to result in adequate illumination of the light sensing element so that even very small particles may be measured. In addition, the light emitting diode and photo diode, both being solid state devices, will operate in high shock and vibration environments which would easily damage other light sources. Thus, the sensor of the present invention is relatively rugged in comparison with those of the prior art, while at the same time providing increased sensitivity for measuring smaller particles, and increased accuracy by providing an accurately collimated light source. Another advantage is that when the light emitting diode emits infrared radiation, there can be no algae growth on the windows when water is used as the fluid. In addition, the light emitting diode has long life, an improvement over filament lamps which may burn out.

These and other advantages of the present invention are best understood through the following detailed description of a preferred embodiment, which description references the drawings, in which:

FIG. 1 is an external elevation view of the sensor of the present invention, combined with a block diagram electrical schematic showing a typical prior art driving and sensing circuit used in association with the sensor;

FIG. 2 is a longitudinal sectional view taken along the central axis of the sensor of the present invention showing the construction thereof;

FIG. 3 is a sectional view taken along lines 3—3 of FIG. 2;

FIG. 4 is a sectional view taken along lines 4—4 of FIG. 2;

FIG. 5 is a sectional view taken along line 5—5 of FIG. 2 to show the flow conduit through the sensor;

FIG. 6 is a partial sectional view taken along 6—6 of FIG. 3 and showing the central portion of the sensor, FIG. 6 showing the means by which the entire sensor assembly is aligned and interengaged;

FIG. 7 is a sectional view taken along line 7—7 of FIG. 2 to show the connection of the light emitting diode of the present invention;

FIG. 8 is a partial sectional view of an alternative embodiment of the sensor of the present invention wherein the light source and collimator are preset and non-adjustable; and FIG. 9 is a partial sectional view of an alternative embodiment of the sensor of the present invention wherein a collimating lens is interiorally attached to the light source.

DETAILED DESCRIPTION OF THE PREFERRED EMBODIMENT

Referring initially to FIG. 1, the rugged light emitting diode sensor 11 of the present invention is shown coupled by means of an end connector 13 to a pair of input wires 15,17 which provide power from a power supply 19 for energizing the sensor 11. In addition, the connector 13 provides interconnection for a pair of output signal lines 21,23 which conduct electrical signals providing information regarding the particle sizes measured by the sensor 11. The lines 21 and 23 in a typical sensor configuration are amplified by an amplifier 25 which supplies an amplified pulse signal to a threshold detector 27. The threshold detector 27, in turn, supplies digital information to an output device 29, such as a numerical readout, which gives an indication of the number of particles of various size groupings measured by the sensor 11. In addition, the average level output from the amplifier 25 is supplied to an average level detector 31 which, in turn, controls the power supply 19 so that the intensity of the light source used for measurement within the sensor 11 may be maintained at a constant level using the average level from the amplifier 25 as a feedback signal. This is an advantage if the measured fluid changes optical density or windows in the sensor cloud up or the output level of the light emitting diode changes. Those skilled in the art will recognize that the output of typical light emitting diodes varies with temperature, and therefore this constant level feedback is often needed.

It should be understood that the circuit shown connected in FIG. 1 to the sensor 11 does not specifically form a part of the present invention. Rather, this circuit is typical of those which have been used in the prior art for driving and monitoring sensors used for particle size measurement.

In many applications, it may be desirable to place the sensor 11 of the present invention in a high shock or vibration environment while the electronic circuit elements 19 through 29 are located in a more stable environment.

The sensor 11 is typically provided with a particle-bearing fluid flow stream by means of an input flow pipe or conduit 33 and an output flow pipe or conduit 35. In a typical application, for example, the pipes 33 and 35 may be in series with a hydraulic circuit, for example, a hydraulic line in a large machine employing plural hydraulic actuators. A small portion of the hydraulic fluid flow, as from the pump in the hydraulic system, may be bypassed through the pipes 33 and 35 so that the sensor 11 may be used to monitor the impurity level of the hydraulic fluid. It may then be possible for the operator of the hydraulic equipment to replace the hydraulic fluid when the particle size and quantity of contaminants within the fluid reaches a level which threatens to damage the pump actuators or other hydraulic equipment. As with the electronic circuit elements of FIG. 1, it will be understood by those skilled in the art that such applications for the sensor 11 are well known.

Referring now to FIG. 2, the details of the sensor 11 which provide its increased sensitivity and ruggedness will be described. The central core of the sensor is formed by a pair of accurately machined metal blocks 37 and 39. The block 39 includes a centrally located cylindrical bore 41 having a first diameter at one end adapted to receive the light sensitive portion of a photo diode 43 and a larger diameter cylindrical section adapted to receive a transparent circular window member 45. The window member 45 conveniently seats against an annular ledge 47 formed between the smaller and larger diameter sections of the bore 41. The window 45 is rigidly attached and sealed to the block 39 and the surface of both the window 45 and block 39 which face the block 37 are accurately machined to provide a flat, smooth surface on that side of the block 39.

In a similar fashion, the block 37 includes a cylindrical through bore 49, including a larger diameter section for mounting a circular transparent window 51 and a smaller diameter section for permitting the application of collimated light through the block 37. As the window 45, the window 51 is rigidly attached and sealed to the block 37 and conveniently seats against a ledge 53 formed at the intersection of the smaller and larger diameter sections of the bore 49. The side of the window 51 opposite the ledge 53 and the adjacent surface of the block 37 form a uniform, flat surface.

While the window 51 is transparent, as specifically shown in FIG. 4, the face of the window 51 adjacent the block 39 is covered with an opaque material 55, in all areas except an accurately defined slit or line 57, which is left transparent. Thus, light which passes through the window 51 can pass through the face adjacent the block 39 only through a very narrow slit 57.

Clamped in position between the blocks 37 and 39 are a pair of shims 59 and 61. As best shown in FIG. 5, each of these shims 59,61 includes a truncated triangular face 63 and 65, respectively, positioned adjacent one another so that a pair of flat sides 67 and 69, respectively, are positioned adjacent one another to form a very narrow, straight flow path 71. This flow path 71, as shown in FIG. 5, is oriented at right angles relative the slit 57.

Together, the slit 57 and flow path 71 form a small, rectangular light path. Thus, the only light entering the blocks 37,39 at the cylindrical passage 49 and passing through to the cylindrical passage 41, is that which passes through both the slit 57 and the flow channel 71. Since the flow channel 71 itself forms a limitation on the light path in one dimension, all particles which flow through the flow path 71 must affect the light path through the blocks 37,39, and thus all particles in the flow path form a part of the measurement sample.

Positioned adjacent the blocks 37 and 39, as well as the shims 59 and 61, are a pair of pipe support blocks 73 and 75. The block 73 includes a central cylindrical aperture having a smaller diameter section 77 and a large diameter section 79. The small diameter section 77 interfaces with the space between the shims 59 and 61 to conduct fluid to that space for measurement. The larger diameter section 79 is threaded to receive the inlet pipe 33 (FIG. 1) which supplies fluid to be monitored to the sensor 11.

In a similar manner, the block 75 includes a central aperture having a small diameter section 81 for conducting fluid from the space between the shims 59 and 61 and a large diameter section 83 for threaded connection to the output conduit 35 (FIG. 1) for conducting fluid away from the sample flow channel.

As shown in FIGS. 2, 4, and 5, four or more bolts 85 interconnect the blocks 37 and 39 and pass through holes in the shims 59 and 61, so that these four elements clamp together as a rigid unit. As specifically shown in FIG. 4 in phantom lines, plural bolts 87 connect the block 73 to the blocks 37 and 39 and a plurality of bolts 89 connect the block 75 to the blocks 37 and 39, so that the entire central core of the sensor 11 becomes a rigid, flow conduit unit including the threaded apertures 79 and 83 in sealed, fluid communication with the central flow conduit 71.

This rigid assembly, called a microcell, becomes, in turn, a subassembly for a second rigid assembly comprising this central flow conduit section, a pair of end plates 91 and 93, a support block 95, and a position adjustment block 97. As is particularly shown in FIGS. 3 and 6, a pair of through bolts 99 and 101 pass through apertures in each of the elements 97, 93, 37, 59, 61, 39, and 91, and are threaded into the block 95 to rigidly interconnect the entire assembly. In order to assist in this assembly, a pair of pilots, 103 and 105, pass through this same series of members, closely, but slidingly fitting in each of the members with the exception of the block 95, in which the pilots are frictionally engaged. These pilots 103,105 assist in the assembly of this combination of parts prior to insertion of the bolts 99 and 101. The assembly which is held together by the bolts 99 and 101 forms the primary base for the entire sensor 11, including the main flow channel and the adjustment block 97 used for mounting and adjusting the lens assembly.

The adjustment block 97 comprises a machined, rectangular, metallic block which includes a large central bore 107 sized to slidingly receive a lens assembly 109 which may, for example, be any of many readily available, precision microscope objective lens assemblies.

In the particular embodiment shown in FIG. 2, the microscope objective lens assembly 109 includes plural lenses arranged to provide a collimation of a point light source positioned at the focal point of the system. This collimation results in parallel rays of light being generated in the lens system 109 for illumination of the cylindrical aperture 49 and the flow channel 71.

It has been found advantageous to utilize a microscope objective lens which has a numerical aperture which is less than one. In the preferred embodiment, shown in FIGS. 2 through 7, the numerical aperture of the lens is 0.5. It will be appreciated by those skilled in the art that the microscope objective lens 109 is of common construction and is available from many sources of microscope parts. Its use in an application, such as that shown in FIGS. 2-7, is advantageous since the use of a standard lens system reduces cost while at the same time assuring the highest quality of optical system available.

In order for the lens system 109 to provide a perfectly collimated light beam for illumination of the flow channel 71, it is important that the point light source used in the system be located as accurately as possible at the focal point of the lens system 109. The necessary adjustment for assuring this location is provided by cooperation of the adjustment block 97 and a yoke 111, as is described below.

Closely fitting around the adjustment block 97 is a U-shaped yoke 111 which includes a pair of extending legs 113 and 115 and a connecting web portion 117. The web portion 117 includes a central aperture 119 which receives the threaded stud 121 of a relatively high power light emitting diode 123. The light emitting diode 123 is clamped at the central aperture 119 by a nut 125 and a spacer block 127. As is clearly shown in FIG. 7, the function of the spacer block 127 is to accurately position the light emitting diode 123 at the axis of the lens system 109. Thus, each of four separate screws 129 may be threaded into or out of the yoke 111 to position and hold the spacer block 127. The spacer block 127 includes a central aperture 131 which closely receives the threaded shank 121 of the light emitting diode 123. Thus, by adjusting the screws 129, it is possible, before tightening of the nut 125 of the light emitting diode 123, to accurately axially align the light emitting diode 123 with the axis of the lens system 109.

From FIG. 7, it can be seen that the end of the yoke member 111 opposite the legs 113 and 115, includes a relatively large circular aperture 133 designed to receive the spacer block 127 and to permit a substantial degree of adjustment in the position of the spacer block 127.

Once the light emitting diode 123 has been axially adjusted and located, as described above, it is necessary that it be located at a position along the axis of the lens system 109 to accurately place its point light source at the focal point of the lens system 109. This is accomplished by sliding the U-shaped yoke member 111 along the adjustment block 97 and, once the focal point is accurately adjusted, tightening a plurality of screws 135 to rigidly interconnect the U-shaped yoke 111 and the adjustment block 97. This, of course, rigidly interconnects the yoke 111 and light emitting diode 123 to the central core of the sensor 11.

The light emitting diode 123 is provided with wiring tabs 137 and 139. The tab 137 is typically clamped under the nut 125. These tabs 137,139 are advantageously aligned above one another so that wires connected these tabs may pass through an aperture 141 (FIG. 6) which extends throughout the entire length of the assembly. The wires are connected to a printed circuit board 143 which is mounted on the support block 95 by means of plural screws 145 and insulating spacers 147. Because of the location of the photodiode 43, it may be directly wired, as shown by the wires 149, to the printed circuit board 143. The printed circuit board is then, in turn, connected by means of plural wires 151 to the connector 13, which supplies power for the light emitting diode 123 and receives signals from the photodiode 43.

The photodiode 43 is mounted in the assembly through a frictional engagement between a cylindrical body portion 152 thereof and a central bore 154 in the support block 95.

The printed circuit board 143 in the preferred embodiment includes an initial amplification stage, so that the signals provided by the photodiode 43 may be amplified before leaving the shielded enclosure of the sensor 11.

As is best shown in FIGS. 1 and 2, the support block 95 and U-shaped yoke 111 are used to support a pair of sheet metal covers 153 and 155, each of which is cup-shaped and is attached to its supporting structure by plural screws 157. These covers exclude foreign matter from the sensor, protect its part from abuse, and shield the electrical wires and amplifier within the sensor.

It will be appreciated by those skilled in the art that, prior to the present invention, it has been thought impossible to use a light emitting diode as a light source for accurately measuring small particles in a sensor, such as that which is shown here. Specifically, the sensor is useful in measuring particles having diameters of a micron or more, and this is normally thought to require extremely high illumination levels not possible with a light emitting diode. Those elements of the present invention which permit this relatively low level illumination source to be used in this application, are the high quality optical system provided by the microscope objective lens 109, the accurate collimation of the point light source provided by the light emitting diode 123 through this lens system 109, and the use of the slit 57 and flow channel 71 to provide boundaries for the light path. All of these features combine, in the present invention, to provide a highly accurate and reliable, rugged sensor which may be used in high vibration and shock environments without damaging the sensor 11.

It is also an important feature of the present invention that the accurate collimation of the point light source permits an extremely accurate measurement of particles in the flow channel 71 to provide output electrical pulses that are very uniform and repeatable. Collimation assures that shadows cast by particles on the photo diode 43 will be precisely the same size as the particles themselves.

In addition to the advantages already stated, it is worth noting that the light emitting diode produces very little heat, which heat might otherwise restrict the application of a sensor of this type, and also that the light emitting diode has fewer aging problems than does a filament bulb, so that a long life, and relatively steady level of illumination, can be expected from this light source.

Referring to FIGS. 8 and 9, there are shown two alternative embodiments of the present invention wherein the assembly of the adjustment block 97 and U-shaped yoke 111 is replaced by a light source-collimator module 201 and 251, respectively. In these two alternative embodiments, the light emitting diode and lens assembly is provided as a factory pre-adjusted unit module which is extremely suitable for in-field modification of the sensor and substantially reduces overall sensor costs.

Referring to the embodiment of FIG. 8, the module 201 comprises a rectangular block 203 having a threaded central aperture 205 and an enlarged central bore 207 extending partially therethrough. Axially aligned and disposed within the enlarged bore 207 adjacent one end thereof is a relatively high power light emitting diode 211 having a threaded stud 213 which is threaded into one end of the small central aperture 205. A short, flat head screw 223 is threaded into the other end of the small aperture 205 to prevent any accumulation of dirt particles within the aperture itself.

The bore 207 is sized to slidingly receive a cylindrical lens 209 which adequately collimates the light from the light emitting diode 211. The lens 209 is positioned at the focal point of the light emitting diode 211 and is secured in position by the tightening of a pair of small set screws (not shown) which extend from opposite sides of the module block 203 into the enlarged bore 207.

A small keyway-like channel 213 extends throughout the length of the enlarged bore 207 and forms a small cavity 215 at one end thereof. An electrical connector 217, which is soldered at one end to the wiring tab 219 of the light emitting diode 211 and routed through the channel 213 and cavity 215 and then passed through aperture 141 (shown in FIG. 6) for subsequent connection to the printed circuit board 143 (as shown in FIG. 6).

The module 201 is aligned and securely held against the end plate 93 by a pair of bolts (99 and 101, as shown in FIG. 3) which extend through a pair of apertures (not shown) in the module block 203 and are threaded into the block 95 (as shown in FIG. 6).

Additionally, to electrically shield and prevent any dirt accumulation within the sensor, the module 201 is provided with a sheet metal cover 221 which is attached to the module 201 by two machine screws (not shown) which extend into the module block 203.

Referring to the embodiment of FIG. 9, the module 250 comprises a rectangular block 251 which includes a small central aperture 253 and an enlarged central bore 255 which extends partially therethrough.

A light emitting diode 257 having a threaded stud 259 is axially located within the enlarged bore 255 by threading the stud 259 into the small central aperture 253. In this embodiment the light emitting diode 257 is provided with an integrally attached cone-like optic lens 260 which protrudes axially from the front face 261 of the light emitting diode 257 into the bore 49 of the block 37. This lens 260 substantially focuses the light from the light emitting diode 259 thereby eliminating the need of any microscope objective lens system.

As with the embodiment of FIG. 8, the module 250 is aligned and abutted against the end plate 93 by a pair of bolts 99 and 101 (as shown in FIG. 3) which extend through the module block 251 and are threaded into block 95 (as shown in FIG. 3) thereby forming a rigid assembly between the module 250 and the rest of the sensor.

Extending radially outward from the enlarged bore 255 is a small recess 263. This recess joins a small aperture 265 which extends axially through the length of the module block 251. An electrical connector 267 is threaded through the aperture 265 and recess 263 and connected to the solder tab 269 of the light emitting diode 257. The solder tab is sleeved in a conventional manner to prevent any electrical shorting during high vibration operation.

A small flat head screw 271 is threaded into the small central aperture 253 adjacent one end of the module block 251 and a sheet metal cover 275 enwraps the module 250 to electrically shield and prevent dirt accumulation within the sensor.

The alternative embodiments of FIGS. 8 and 9 operate substantially in the same manner as the preferred embodiment of FIG. 1 except that, due to the nonadjustable nature of both the light emitting diode's axial position and microscope objective lens system, the light collimation accuracy is somewhat diminished. This diminished light collimation produces a moderate loss in light intensity thereby reducing the accuracy of the particle size measurements of the sensor.

This loss of measurement accuracy is maintained at a minimum level in the embodiment of FIG. 8 due to the factor, adjustment of the lens 209 relative the point source of the light emitting diode 211 within the enlarged central bore 207. However, the measurement accuracy is further decreased in the embodiment of FIG. 9 wherein, due to the increased inaccuracy in light collimation of the cone-like lens 259 and its fixed nonadjustable focal length, fine tuning of the sensor is impossible.

However, the applicant has discovered that, even with this somewhat diminished measurement accuracy, the embodiments of FIGS. 8 and 9 provide a suitable lower cost sensor which can be effectively utilized in extremely high vibration applications which previously would have prevented the use of any sensoring device.

What is claimed is:

1. A rugged sensor for measuring the size of particles carried by a fluid stream flowing through a conduit, comprising:
    a light emitting diode which provides a point source of illumination;
    an optical system positioned adjacent said light emitting diode with its focal point at said diode point source, said optical system providing a parallel beam of light from said light emitting diode;
    a flow channel, connected to said conduit with a portion of said channel having a width narrow relative to the width of said conduit, said narrow portion of said flow channel formed between a pair of opposite wall surfaces, and located for illumination by said beam of light;
    a wall member forming a third wall of said narrow portion of said flow channel, said wall member being opaque except for a transparent slit, narrow in width relative to its length, and oriented perpendicular to said narrow portion of said flow channel and said pair of opposite wall surfaces, said narrow slit located for illumination by said beam of light, said narrow portion of said flow channel and said narrow slit combining to form a restricted light path which permits only a small segment of said parallel beam of light to pass through said narrow portion of said flow channel, said segment limited in one dimension by said narrow width of said narrow portion of said flow channel and in a second imension by said narrow width of said slit;
    said conduit conducting particle bearing fluid to said flow channel; and
    a light sensitive detector positioned adjacent said narrow portion of said flow channel for illumination by said beam of light, the electrical output of said detector being responsive to particles in said narrow portion of said flow channel.

2. A rugged sensor, as defined in claim 1, additionally comprising:
    means mounting said optical system and said light emitting diode, said means permitting accurate relative adjustment of said optical system and said light emitting diode to precisely locate the point source of said light emitting diode at the focal point of said optical system.

3. A rugged sensor, as defined in claim 1, wherein said wall member comprises a transparent glass wall section having an opaque coating on one face of said glass, said opaque coating covering one surface of said glass except for a transparent slit oriented perpendicular to said flow channel.

4. A rugged sensor, as defined in claim 1, wherein said flow channel opposite wall members each comprise a shim, said sensor additionally comprising:
    a second pair of wall members abutting against said pair of shims so that with said pair of shims a flow channel is provided, said shims being adjusted in position to provide a very narrow flow channel through said sensor.

5. A rugged sensor, as defined in claim 1, additionally comprising:
    a sensor housing surrounding said light emitting diode, said optical system, and said light sensitive detector; and
    an electronic amplifier mounted within said housing and connected to said light sensitive detector for amplifying signals produced by said detector in response to particles in said flow channel, the location of said amplifier within said housing shielding said amplifier and the wires interconnecting said detector and said amplifier from electronic interference.

6. A rugged sensor for measuring the size of particles carried by a fluid stream, comprising:
    a light emitting diode which provides a point source of illumination;
    an optical system positioned adjacent said light emitting diode with its focal point at said diode point source, said optical system providing a parallel beam of light from said light emitting diode and wherein said optical system comprises a lens which is mounted directly upon said light emitting diode;
    a flow channel formed between a pair of opposite wall surfaces and located for illumination by said beam of light;
    a wall member forming a third wall of said flow channel, said wall member being opaque except for a transparent slit oriented perpendicular to said flow channel and said pair of opposite wall surfaces, said slit located for illumination by said beam of light;
    means conducting particle bearing fluid to said flow channel; and
    a light sensitive detector positioned adjacent said flow channel for illumination by said beam of light, the electrical output of said detector being responsive to particles in said flow channel.

7. A high accuracy sensor for measuring the size of particles carried by a fluid stream through a conduit, comprising:
    a source of light;
    a flow channel connected to said conduit to receive particle bearing fluid, said channel having a portion which is narrow in comparison to said conduit, said narrow portion of said flow channel including a pair of opposite side walls which are opaque and form a boundary, which is narrower than the beam of light from said light source in a direction perpendicular to said flow channel; and a third wall of said flow channel contiguous with said pair of opposite side walls, said third wall being opaque except for a transparent slit which is narrow in width relative to its length, narrower than said beam of light, and oriented in a direction substantially normal to the direction of flow of said flow channel, said slit and said opposite side walls forming two-dimensional boundaries, which are narrow in both dimensions in comparison to said beam of light, for occluding all but a small portion of said beam of light to provide a restricted light path through said narrow portion of said flow channel.

8. A high accuracy sensor, as defined in claim 7, wherein said source of light comprises a light emitting diode.

9. A high accuracy sensor, as defined in claim 8, wherein said source of light additionally comprises a collimating lens system located with its focal point at said light emitting diode, said collimating lens system providing a parallel beam of light for illuminating said flow channel.

10. A high accuracy sensor, as defined in claim 7, wherein said third wall of said flow channel is formed of glass, said glass including an opaque coating on all of one surface except for a narrow transparent line oriented in a direction substantially normal to said flow channel.

11. A high accuracy sensor, as defined in claim 10, wherein said opaque coating on said glass wall is on a surface of said glass wall which is abutted against said pair of opposite side walls.

12. A high accuracy sensor, as defined in claim 7, additionally comprising:

a fourth transparent wall of said flow channel contiguous with said pair of opposite side walls; and a light detector positioned adjacent said fourth transparent wall.

13. A high accuracy sensor, as defined in claim 12, wherein said pair of opposite side walls each comprise the edge of a shim, said shims abutted between said third and fourth walls.

14. A rugged sensor for measuring the size of particles carried by a fluid stream, comprising:

a light emitting diode providing a point source of light;

a microscope objective lens system for collimating light from said point source, said lens system having a low numerical aperture;

means for adjusting the relative position of said light emitting diode and said lens system to accurately position said light emitting diode point source at the focal point of said lens system;

a flow channel for said fluid stream positioned to be illuminated by said collimated light; and a detector mounted to respond to light from said lens system which has passed through said flow channel.

15. A rugged sensor, as defined in claim 14, wherein a pair of opposite walls of said flow channel are transparent only for a very short length of said flow channel, said short transparent length and walls of said flow channel together forming boundaries which determine the amount of said collimated light which will pass through said flow channel.

16. A rugged sensor, as defined in claim 14, wherein said means adjusting the relative position of said light emitting diode and said lens system comprises:

a U-shaped yoke supporting said light emitting diode;

a block supporting said microscope objective lens system, said U-shaped yoke fitting around and sliding relative said block; and means for rigidly interconnecting said U-shaped yoke and said block to fix the relative position of said light emitting diode and said microscope objective lens system.

17. A rugged sensor, as defined in claim 14, wherein the numerical aperture of said microscope objective lens is very low (less than 1.0).

18. A rugged sensor, as defined in claim 14, wherein said detector is mounted on the opposite side of said flow channel from said light emitting diode and said microscope objective lens system, said light emitting diode, said lens system, said flow channel, and said detector all mounted along a single axis so that light from said light emitting diode and lens system can be interrupted by particles in said flow channel to reduce the level of light falling on said detector.

* * * * *